US012577199B2

(12) United States Patent
Takashita

(10) Patent No.: US 12,577,199 B2
(45) Date of Patent: Mar. 17, 2026

(54) METHOD OF MANUFACTURING FLUORINE-CONTAINING COMPOUND

(71) Applicant: AGC Inc., Tokyo (JP)

(72) Inventor: Ryuta Takashita, Chiyoda-ku (JP)

(73) Assignee: AGC Inc., Tokyo (JP)

( * ) Notice: Subject to any disclaimer, the term of this patent is extended or adjusted under 35 U.S.C. 154(b) by 967 days.

(21) Appl. No.: 17/698,102

(22) Filed: Mar. 18, 2022

(65) Prior Publication Data

US 2022/0204444 A1 Jun. 30, 2022

Related U.S. Application Data

(63) Continuation of application No. PCT/JP2020/035360, filed on Sep. 17, 2020.

(30) Foreign Application Priority Data

Sep. 20, 2019 (JP) ................................ 2019-171578

(51) Int. Cl.
*C07C 309/04* (2006.01)
*C07C 17/263* (2006.01)

(52) U.S. Cl.
CPC ........ *C07C 309/04* (2013.01); *C07C 17/2632* (2013.01)

(58) Field of Classification Search
USPC .......................................................... 562/530
See application file for complete search history.

(56) References Cited

U.S. PATENT DOCUMENTS

2007/0123734 A1 5/2007 Nakamura et al.
2013/0048913 A1 2/2013 Tanaka et al.
2014/0302332 A1 10/2014 Murotani et al.
2020/0339492 A1 10/2020 Ivanov Bichovski et al.

FOREIGN PATENT DOCUMENTS

CN 103265403 A 8/2013
JP 10-204004 A 8/1998
JP 11-228454 A 8/1999
JP 2004-051595 A 2/2004
JP 2008-21 4199 A 9/2008
JP 2013-060417 A 4/2013
JP 2018-043940 A 3/2018
WO WO 2005/075384 A1 8/2005
WO WO 2013/121984 A1 8/2013
WO WO 2018/228975 A1 12/2018

OTHER PUBLICATIONS

Machine translation CN103265403.*
Chu-Ting Yang, et al., "Copper-Catalyzed Cross-Coupling of Non-activated Secondary Alkyl Halides and Tosylates with Secondary Alkyl Grignard Reagents", Journal of the American Chemical Society, Jul. 11, 2012, vol. 134, No. 27, pp. 11124-11127, XP93080832.
Peter J. Stang, et al., "Perfluoroalkanesulfonic Esters: Methods of Preparation And Applications In Organic Chemistry", Synthesis, Jan. 1, 1982, pp. 85-126, XP000919260.
International Search Report issued Nov. 2, 2020 in PCT/JP2020/035360 filed on Sep. 17, 2020, 3 pages.
Umemoto, "Electrophilic Perfluoroalkylating Agents", Chem. Rev. 1996, 96, pp. 1757-1777.

* cited by examiner

*Primary Examiner* — Ana Z Muresan
(74) *Attorney, Agent, or Firm* — Oblon, McClelland, Maier & Neustadt, L.L.P.

(57) ABSTRACT

The present invention is directed to providing a method of manufacturing a fluorine-containing compound according to which a fluorine-containing compound is manufactured under a relatively moderate reaction condition by use of a readily available compound. A method of manufacturing a fluorine-containing compound includes reacting a compound having a partial structure expressed by a formula (a) below with a Grignard reagent in the presence of a transition metal compound, $$—CF_2—CH_2\text{-}L \quad (a)$$

wherein L is a sulfonate group.

6 Claims, No Drawings

METHOD OF MANUFACTURING FLUORINE-CONTAINING COMPOUND

INCORPORATION BY REFERENCE

This application is based upon and claims the benefit of priority from Japanese Patent Application 2019-171578 filed on Sep. 20, 2019, and PCT application No. PCT/JP2020/035360 filed on Sep. 17, 2020, the disclosure of which is incorporated herein in its entirety by reference.

BACKGROUND

The present invention relates to methods of manufacturing fluorine-containing compounds.

BACKGROUND ART

Fluorine compounds are used in a variety of fields, including agricultural chemicals, medicines, and intelligent materials, and there exists a demand for a simpler method of synthesizing fluorine compounds of various structures.

Various studies are being done on methods of synthesizing compounds having a structure in which an alkyl group is bonded to a fluoroalkyl group.

For example, Japanese Unexamined Patent Application Publication No. 2018-43940 discloses a method of manufacturing a fluorine-containing compound, according to which perfluoroalkyl bromide is added to an olefin compound by radical reaction.

Examples in International Patent Publication No. WO2018/228975 disclose a method in which a Grignard reagent is reacted with $R^f$—$CF_2CH_2CH_2$-1 ($R^f$ is a perfluoroalkyl group) serving as an electrophilic reagent.

Meanwhile, Teruo Umemoto, "Electrophilic Perfluoroalkylating Agents," Chem. Rev. 1996, 96, 1757-1777. discloses, as an electrophilic perfluoroalkylating agent, a compound expressed by the following formula.

[Chem. 1]

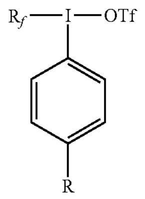

In the above, $R_f$ is n-$C_mF_{2m+1}$, Tf is $SO_2CF_3$, and R is H or F.

SUMMARY

The technique according to Patent Literature 1 above is not suitable for synthesizing a compound having a carbon-carbon double bond since olefin is the one that reacts. This technique also limits the types of electrophilic reagents. Moreover, since the product may further undergo radical reaction to be telomerized, and a large variety of by-products are produced.

The electrophilic reagent disclosed in Patent Literature 2 above is not readily available.

Meanwhile, the electrophilic perfluoroalkylating agent disclosed in Non Patent Literature 1 above needs to be synthesized in a multi-stage process, which leads to a low yield and makes this electrophilic reagent expensive.

The present invention is directed to providing a method of manufacturing a fluorine-containing compound according to which a fluorine-containing compound is manufactured under a relatively moderate reaction condition by use of a readily available compound.

Solution to Problem

As to configurations that achieve the above, the present invention relates to the following [1] to [8].

[1] A method of manufacturing a fluorine-containing compound, the method comprising:

reacting a compound having a partial structure expressed by a formula (a) below with a Grignard reagent in the presence of a transition metal compound, $$—CF_2—CH_2\text{-}L \qquad \text{Formula (a)}$$

wherein L is a sulfonate group.

[2] The method of manufacturing a fluorine-containing compound according to claim 1, wherein the compound having the partial structure expressed by the formula (a) is a compound expressed by a formula (A1) or a formula (A2) below, $$G^1\text{-}CF_2—CH_2\text{-}L \qquad \text{Formula (A1)}$$

$$L\text{-}CH_2(—CF_2\text{-}G^2)_n\text{-}CF_2—CH_2\text{-}L \qquad \text{Formula (A2)}$$

wherein $G^1$ is a monovalent group having a (poly)oxyfluoroalkylene chain, a hydrogen atom, an alkyl group, or a fluoroalkyl group, $G^2$ is a divalent group having a (poly)oxyfluoroalkylene chain, a single bond, an alkylene group, or a fluoroalkylene group, L is a sulfonate group, and a plurality of L's in the formula (A2) may be identical to or different from each other, and n is 0 or 1.

[3] The method of manufacturing a fluorine-containing compound according to [2], wherein in the formula (A1), $G^1$ is a monovalent group having a (poly)oxyfluoroalkylene chain or a perfluoroalkyl group.

[4] The method of manufacturing a fluorine-containing compound according to [2], wherein in the formula (A2), n is 0, or n is 1, and $G^2$ is a divalent group having a (poly)oxyfluoroalkylene chain, a single bond, or a perfluoroalkylene group.

[5] The method of manufacturing a fluorine-containing compound according to any one of [1] to [4], wherein the Grignard reagent is expressed by a formula (B) below, $$R—MgX \qquad \text{Formula (B)}$$

wherein R is a hydrocarbon group that may include a substituent and may include a heteroatom within a carbon chain, and X is a halogen atom.

[6] The method of manufacturing a fluorine-containing compound according to [5], wherein the Grignard reagent is expressed by a formula (B1) below, $$R^1—CH_2—MgX \qquad \text{Formula (B1)}$$

wherein $R^1$ is a hydrogen atom or a hydrocarbon group that may include a substituent and may include a heteroatom within a carbon chain, and X is a halogen atom.

[7] The method of manufacturing a fluorine-containing compound according to any one of [1] to [6], wherein L is a triflate group.

[8] The method of manufacturing a fluorine-containing compound according to any one of [1] to [7], wherein the transition metal compound includes copper.

Advantageous Effects of Invention

The present invention can provide a method of manufacturing a fluorine-containing compound under a relatively moderate condition by use of a readily available compound.

The above and other objects, features and advantages of the present disclosure will become more fully understood from the detailed description given hereinbelow and the accompanying drawings which are given by way of illustration only, and thus are not to be considered as limiting the present disclosure.

DESCRIPTION OF EMBODIMENTS

In the present specification, a partial structure expressed by a formula (a) is referred to as a partial structure (a). Meanwhile, a compound expressed by a formula (A1) is referred to as a compound (A1). This convention applies similarly to compounds expressed by the other formulas.

(Poly)oxyfluoroalkylene is a collective term for oxyfluoroalkylene and polyoxyfluoroalkylene.

A perfluoroalkyl group refers to a group where all the hydrogen atoms in an alkyl group are replaced by fluorine atoms. Meanwhile, a fluoroalkyl group is a collective term for a partial fluoroalkyl group and a perfluoroalkyl group. A partial fluoroalkyl group refers to an alkyl group where one or more hydrogen atoms are replaced by a fluorine atom or fluorine atoms and that includes one or more hydrogen atoms.

In other words, a fluoroalkyl group is an alkyl group having one or more fluorine atoms.

"From" and "to" indicating a range of numerical values mean that this range includes the respective numerical values following "from" and "to" as the lower limit and the upper limit.

Method of Manufacturing Fluorine-Containing Compound

A method of manufacturing a fluorine-containing compound according to the present invention (also referred to below as the present manufacturing method) includes reacting a compound having a partial structure expressed by a formula (a) below with a Grignard reagent in the presence of a transition metal compound.

When the Grignard reagent is expressed by a formula (B) below, the above reaction is expressed by a scheme (1) below.

$$R—MgX \qquad \text{Formula (B)}$$

In the above formula, R is a hydrocarbon group that may include a substituent and may include a heteroatom within a carbon chain, and X is a halogen atom.

$$—CF_2—CH_2\text{-}L+R—MgX \rightarrow —CF_2—CH_2—R \qquad \text{Scheme (1)}$$

In the above, the symbols in the scheme (1) are as described above.

According to the present manufacturing method, a sulfonate group is used as a leaving group L of the partial structure (a) that reacts with the Grignard reagent, and thus the reaction of the above scheme (1) can be carried out under a relatively moderate reaction condition. In the following, each configuration of the present manufacturing method will be described in detail.

L in the partial structure (a) is a sulfonate group (—O—$SO_2$—$R^2$) and leaves through a reaction with the Grignard reagent. $R^2$ is an organic group. Specific examples of the sulfonate group include a tosylate group (OTs), a mesylate group (OMs), a triflate group (OTf), and a nonaflate group (ONf). Among the above, a triflate group is preferable from the standpoint of the reaction yield of the scheme (1).

A compound having the partial structure (a) (also referred to below as a compound (A)) is a compound having one or more partial structures (a). From the standpoint of the reaction yield, the number of the partial structures (a) within the compound (A) is preferably from 1 to 6, more preferably from 1 to 4, or even more preferably from 1 to 2.

The structure of the compound (A) may be selected, as appropriate, in accordance with, for example, the intended use of the fluorine-containing compound obtained through the present manufacturing method.

Examples of the compound (A) having n5 partial structures (a) include a compound expressed by a formula (An5) below.

$$G(—CF_2—CH_2\text{-}L)_{n5} \qquad \text{Formula (An5)}$$

In the above formula,

G is a hydrogen atom (where n5=1) or an organic group with a valency of n5, n5 is an integer greater than or equal to 1, and L is as described above.

The organic group in G is a substituent that includes one or more carbon atoms. Examples of the organic group include a hydrocarbon group that may include a substituent and may include a heteroatom or a bond of other than a hydrocarbon group within a carbon chain or at a terminal that bonds to the partial structure (a).

Examples of such a hydrocarbon group include a linear or branched alkyl group, a cycloalkyl group, an aryl group, or a combination thereof. The hydrocarbon group may include a double bond or a triple bond within a carbon chain. Examples of the combination include a combination where an alkyl group and an aryl group are bonded to each other directly, via a heteroatom, or via a bond of other than a hydrocarbon group.

Examples of the heteroatoms include an oxygen atom, a nitrogen atom, a sulfur atom, and a silicon atom.

The heteroatom may constitute a part of a ring structure. Of the heteroatoms, a nitrogen atom, a sulfur atom, and a silicon atom may constitute a branch point that bonds to three or more carbon atoms.

Examples of the bond of other than a hydrocarbon group include an amide bond, a urea bond, and a urethane bond.

Examples of the substituent that may be included in the hydrocarbon group include a halogen atom, a hydroxyl group, an amino group, a nitro group, and a sulfo group. From the standpoint of the stability of the compound according to the present manufacturing method, a halogen atom is preferable, and in particular a fluorine atom is more preferable.

When the organic group includes a ring structure, as in a cycloalkyl group or an aryl group, examples of such a ring structure include an aliphatic ring of from 3 to 8 members, an aromatic ring of from 6 to 8 members, a hetero ring of from 3 to 8 members, or a fused ring consisting of two or more of the above rings. A ring structure expressed by the following formula is preferable.

The ring structure may include as a substituent, for example but not limited to, a halogen atom, an alkyl group that may include an ether bond, a cycloalkyl group, an alkenyl group, an allyl group, an alkoxy group, or an oxo group.

[Chem. 2]

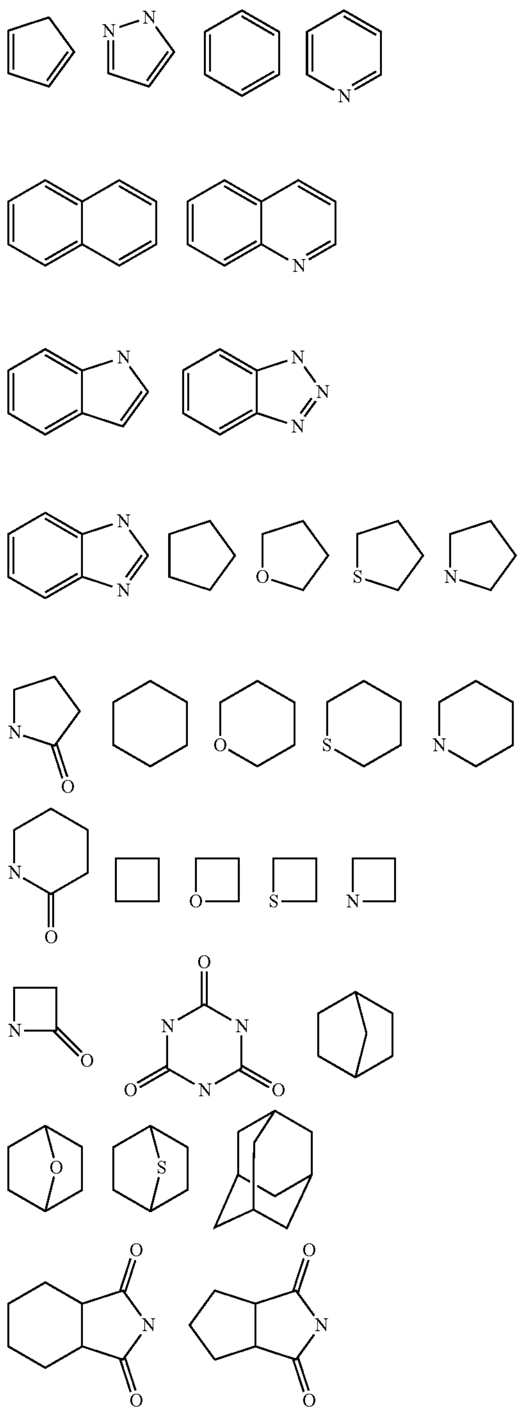

Of the compounds (A), some specific, preferable examples of a compound having a ring structure include the following.

[Chem. 3]

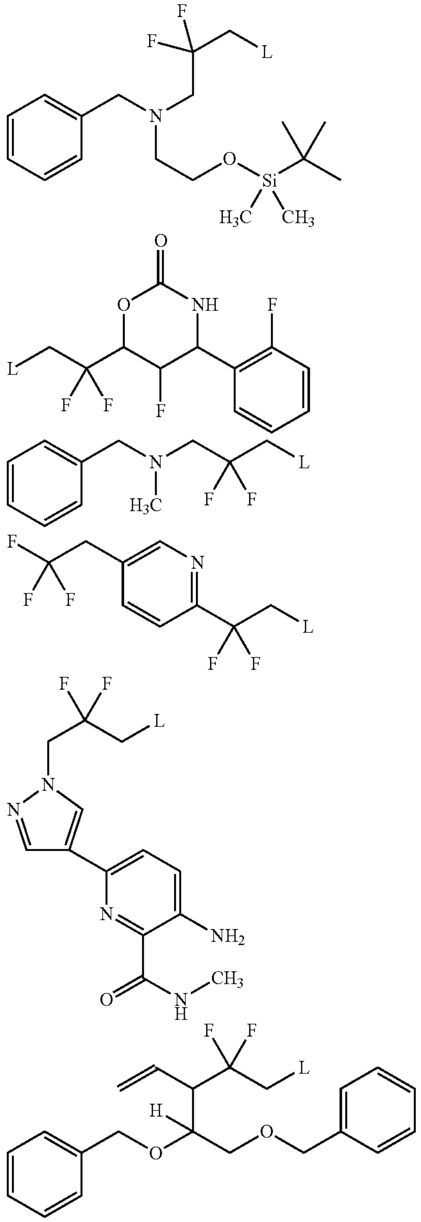

In the above, L is as described above.

From the standpoint of increasing the yield of the present manufacturing method, the above compound (A) is preferably a compound expressed by a formula (A1) or a formula (A2) below.

$G^1$-$CF_2$—$CH_2$-L    Formula (A1)

L-$CH_2$(—$CF_2$-$G^2$)$_n$-$CF_2$—$CH_2$-L    Formula (A2)

In the above formulas, $G^1$ is a monovalent group having a (poly)oxyfluoroalkylene chain, a hydrogen atom, an alkyl group, or a fluoroalkyl group, $G^2$ is a divalent group having a (poly)oxyfluoroalkylene chain, a single bond, an alkylene group, or a fluoroalkylene group, L may be a sulfonate group, and a plurality of L's in the formula (A2) may be identical to or different from each other, and n is 0 or 1.

From the standpoint of, for example, increasing the yield of the present manufacturing method, the carbon number of the alkyl group or the fluoroalkyl group in G' is preferably from 1 to 30, more preferably from 1 to 20, even more preferably from 1 to 10, or particularly preferably from 1 to 6.

In the formula (A1), the monovalent group having a (poly)oxyfluoroalkylene chain in $G^1$ is a fluoroalkyl group that includes —O— at a terminal that bonds to $CF_2$, includes —O— between carbon atoms in a carbon chain having a carbon number of 2 or more, or includes both of the two above. From the standpoint of, for example, the ease of manufacturing, $G^1$ is preferably a structure expressed by a formula (G1-1) below.

$$R^{f0}O—[(R^{f1}O)_{m1}(R^{f2}O)_{m2}(R^{f3}O)_{m3}(R^{f4}O)_{m4}(R^{f5}O)_{m5}(R^{f6}O)_{m6}]—(R^{f7})_{m7}— \quad \text{Formula (G1-1)}$$

In the above, $R^{f0}$ is a fluoroalkyl group having a carbon number of from 1 to 20, $R^{f1}$ is a fluoroalkylene group having a carbon number of 1, $R^{f2}$ is a fluoroalkylene group having a carbon number of 2, $R^{f3}$ is a fluoroalkylene group having a carbon number of 3, $R^{f4}$ is a fluoroalkylene group having a carbon number of 4, $R^{f5}$ is a fluoroalkylene group having a carbon number of 5, $R^{f6}$ is a fluoroalkylene group having a carbon number of 6, $R^{f7}$ is a fluoroalkylene group having a carbon number of from 1 to 6, m1, m2, m3, m4, m5, and m6 each independently represent 0 or an integer greater than or equal to 1, m7 is 0 or an integer of 1, and m1+m2+m3+m4+m5+m6+m7 yields an integer of from 0 to 200.

Herein, the order of bonding of ($R^{f1}O$) to ($R^{f6}O$) in the formula (G1-1) is flexible.

m1 to m6 in the formula (G1-1) represent the respective numbers of ($R^{f1}O$) to ($R^{f6}O$) and do not represent their arrangement. For example, $(R^{f5}O)_{m5}$ indicates that the number of ($R^{f5}O$) is m5 and does not represent the block arrangement structure of $(R^{f5}O)_{m5}$. In a similar manner, the order in which ($R^{f1}O$) to ($R^{f6}O$) are listed does not represent the bonding order of these units.

When m7 is 0, the terminal of $G^1$ that bonds to $CF_2$ is —O—. When m7 is 1, the terminal of $G^1$ that bonds to $CF_2$ is a carbon atom (the carbon atom at the terminal of $R^{f7}$).

Specific examples of $G^1$ include $CH_3$—, $CH_3CH_2$—, $CH_3CH_2CH_2$—, $CH_3CH_2CH_2CH_2$—, $CH_3CH_2CH_2CH_2CH_2$—, $CH_3CH_2CH_2CH_2CH_2CH_2$—, $CF_3$—, $CF_3CF_2$—, $CF_3CF_2CF_2$—, $CF_3CF_2CF_2CF_2$—, $CF_3CF_2CF_2CF_2CF_2$—, $CF_3CF_2CF_2CF_2CF_2CF_2$—, $CF_3CF_2CF_2$—O—$[(CF_2—O)_{m1}(CF_2CF_2—O)_{m2}]$—, $CF_3CF_2CF_2$—O—$CF_2CF_2$—O—$[(CF_2—O)_{m1}(CF_2CF_2—O)_{m2}]$—, $CF_3$—O(—$CF_2CF_2$—O—$CF_2CF_2CF_2CF_2$—$O)_{m8}$—$CF_2CF_2$—O—$CF_2CF_2$—, and F(—$CF_2CF_2CF_2$—$O)_{m3}$—$CF_2$— (in the above, m8 is an integer of from 1 to 100).

In the formula (A1), from the standpoint of, for example, the yield of the present manufacturing method, $G^1$ is preferably a monovalent group having a (poly)oxyfluoroalkylene chain or a perfluoroalkyl group.

From the standpoint of, for example, increasing the yield of the present manufacturing method, the carbon number of the alkylene group or the fluoroalkylene group in $G^2$ is preferably from 1 to 30, more preferably from 1 to 20, even more preferably from 1 to 10, or particularly preferably from 1 to 6.

In the formula (A2), the divalent group having a (poly)oxyfluoroalkylene chain in $G^2$ is a fluoroalkylene group that includes —O— at each of the two terminals that bond to $CF_2$, includes —O— between carbon atoms in a carbon chain having a carbon number of 2 or more, or is a combination of the two above. From the standpoint of, for example, the ease of manufacturing, $G^2$ is preferably a structure expressed by a formula (G2-1) below.

$$—(O)_{m0}—[(R^{f1}O)_{m1}(R^{f2}O)_{m2}(R^{f3}O)_{m3}(R^{f4}O)_{m4}(R^{f5}O)_{m5}(R^{f6}O)_{m6}]—(R^{f7})_{m7}— \quad \text{Formula (G2-1)}$$

In the above, m0 is an integer of 0 or an integer of 1; and $R^{f1}$, $R^{f2}$, $R^{f3}$, $R^{f4}$, $R^{f5}$, $R^{f6}$, $R^{f7}$, m1, m2, m3, m4, m5, m6, and m7 are the same as those in $G^1$ described above. Herein, the order of bonding of ($R^{f1}O$) to ($R^{f6}O$) in the formula (G2-1) is flexible, as given in the description of the formula (G1-1) above.

When m7 is 0, the one terminal of $G^2$ that bonds to $CF_2$ is —O—. When m7 is 1, the one terminal of $G^2$ that bonds to $CF_2$ is a carbon atom (the carbon atom at the terminal of $R^{f7}$). Meanwhile, when m0 is 1, the one terminal of $G^2$ that bonds to $CF_2$ is —O—. When m0 is 0, the one terminal of $G^2$ that bonds to $CF_2$ is a carbon atom (the carbon atom at the terminal of any one of $R^{f1}$ to $R^{f7}$). Herein, m0 and m7 are each independently 0 or 1.

Specific examples of $G^2$ include —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —$CF_2$—, —$CF_2CF_2$—, —$CF_2CF_2CF_2$—, —$CF_2CF_2CF_2CF_2$—, —$CF_2CF_2CF_2CF_2CF_2$—, —$CF_2CF_2CF_2CF_2CF_2CF_2$—, and —O— $[(CF_2—O)_{m1}(CF_2CF_2—O)_{m2}]$—.

Herein, in the formula (A2), when n is 0, the compound (A) is L-$CH_2$—$CF_2$—$CH_2$-L. Meanwhile, in the formula (A2), when n is 1 and $G^2$ is a single bond, the compound (A) is L-$CH_2$—$CF_2$—$CF_2$—$CH_2$-L.

From the standpoint of, for example, the yield of the present manufacturing method, in the formula (A2), n is preferably 0; or n is preferably 1, and $G^2$ is preferably a divalent group having a (poly)oxyfluoroalkylene chain, a single bond, or a perfluoroalkylene group.

Specific, preferable examples of the compound (A) include the following.

[Chem. 4]

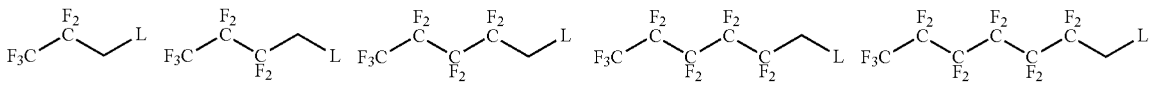

-continued

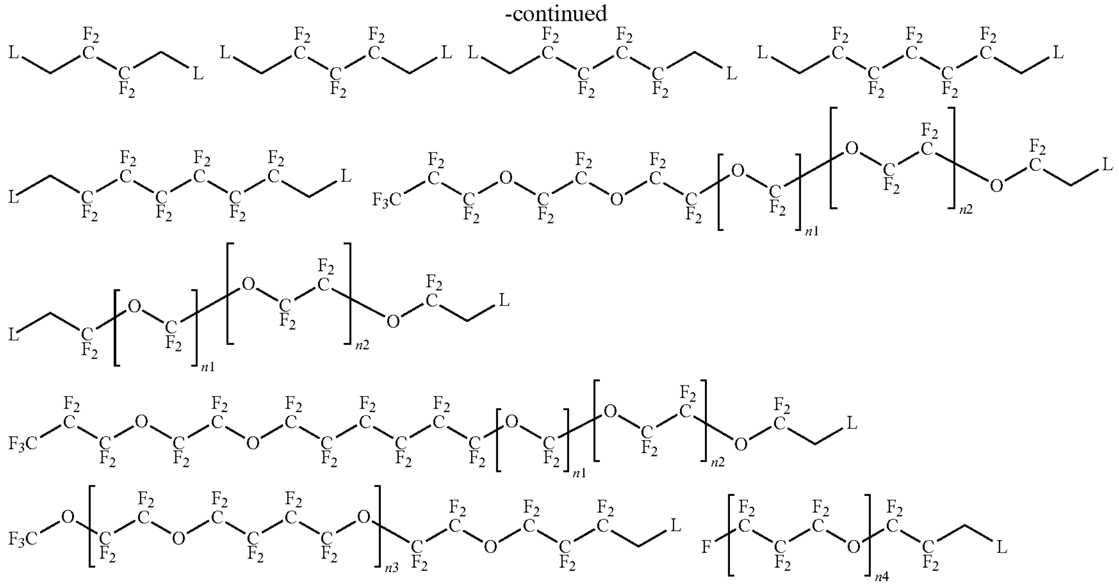

In the above, n1, n2, n3, and n4 are each an integer of from 1 to 100.

Herein, the present manufacturing method can be applied even when $G^1$ is a fluorine atom in the formula (A1), that is, even when the compound (A) is $CF_3$—$CH_2$-L. However, one of the characteristic features of the present manufacturing method is that the method exhibits excellent reactivity for a structure in which two fluorine atoms are bonded to a β carbon with respect to the leaving group L and in which further a carbon chain or the like extends, and the case where $G^1$ is a fluorine atom is excluded.

The compound (A) can be manufactured through, for example, a method in which a compound expressed by a formula (A1-2) or a formula (A2-2) below is reacted with, for example, trifluoromethanesulfonic anhydride, tosyl chloride, or mesyl chloride in the presence of an organic amine compound, such as triethylamine or pyridine to be sulfonated.

$G^1$-$CF_2$—$CH_2OH$ Formula (A1-2)

HO—$CH_2$(—$CF_2$-$G^2$)$_n$-$CF_2CH_2$—OH Formula (A2-2)

In the above, $G^1$, $G^2$, and n in the formulas are as described above.

The Grignard reagent may be one that can react with the partial structure (a) described above. According to the present manufacturing method, from the standpoint of suppressing, for example, a side reaction, the Grignard reagent is preferably a compound expressed by a formula (B) below.

R—MgX Formula (B)

In the above formula, R is a hydrocarbon group that may include a substituent and may include a heteroatom within a carbon chain, and X is a halogen atom.

R can be selected for use, as appropriate, from those having a desired structure to be introduced into the compound (A) described above.

The hydrocarbon group in R may include a heteroatom, may include a substituent, or may include a double bond or a triple bond, with a linear alkyl group, an alkyl group with a branch, a cycloalkyl group, an aryl group, or a group consisting of a combination of the above serving as a base skeleton.

Examples of the heteroatoms include a nitrogen atom (N), an oxygen atom (O), a sulfur atom (S), and a silicon atom (Si). From the standpoint of the stability of the compound, N, O, or S is preferable. For the substituent, a fluorine atom is preferable. From the standpoint of, for example, improving the yield of the present manufacturing method, the carbon number of R is preferably from 1 to 30, more preferably from 1 to 20, or even more preferably from 1 to 15.

From the standpoint of the reactivity, the halogen atom in X is preferably a chlorine atom, a bromine atom, or an iodine atom, and among those, a chlorine atom or a bromine atom is more preferable.

Examples of such a Grignard reagent include a primary alkyl Grignard reagent in which the magnesium-bonding carbon atom is a primary carbon atom, such as methylmagnesium chloride, ethylmagnesium chloride, or allylmagnesium chloride; a secondary alkyl Grignard reagent, such as isopropylmagnesium chloride; a tertiary alkyl Grignard reagent, such as tert-butylmagnesium chloride; an aryl Grignard reagent, such as phenylmagnesium chloride; and vinylmagnesium chloride.

According to the present manufacturing method, from the standpoint of obtaining a target product at high yield, the Grignard reagent is preferably a Grignard reagent expressed by a formula (B1) below.

$R^1$—$CH_2$—MgX Formula (B1)

In the above formula, $R^1$ is a hydrogen atom or a hydrocarbon group that may include a substituent and may include a heteroatom within a carbon chain, and X is a halogen atom. $R^1$ is preferably a residue obtained by removing —$CH_2$ from R.

When the magnesium-bonding carbon atom is a primary carbon atom, the present manufacturing method can be carried out under a relatively mild reaction condition.

Specific, preferable examples of the formula (B1) include the following.
[Chem. 5]
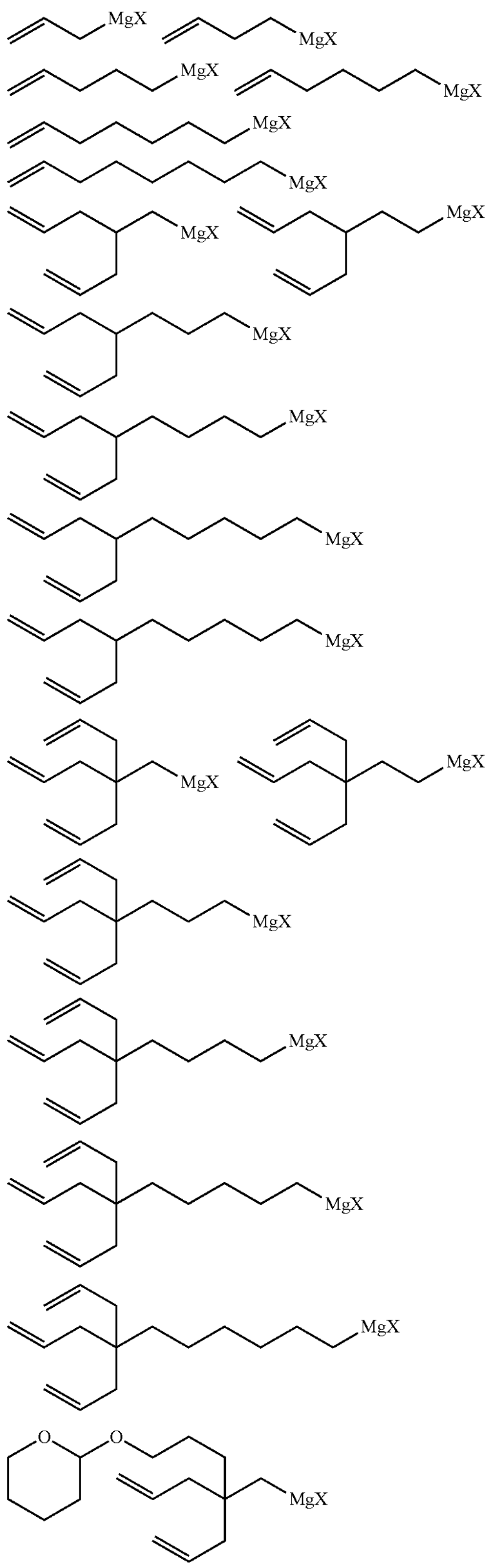
-continued
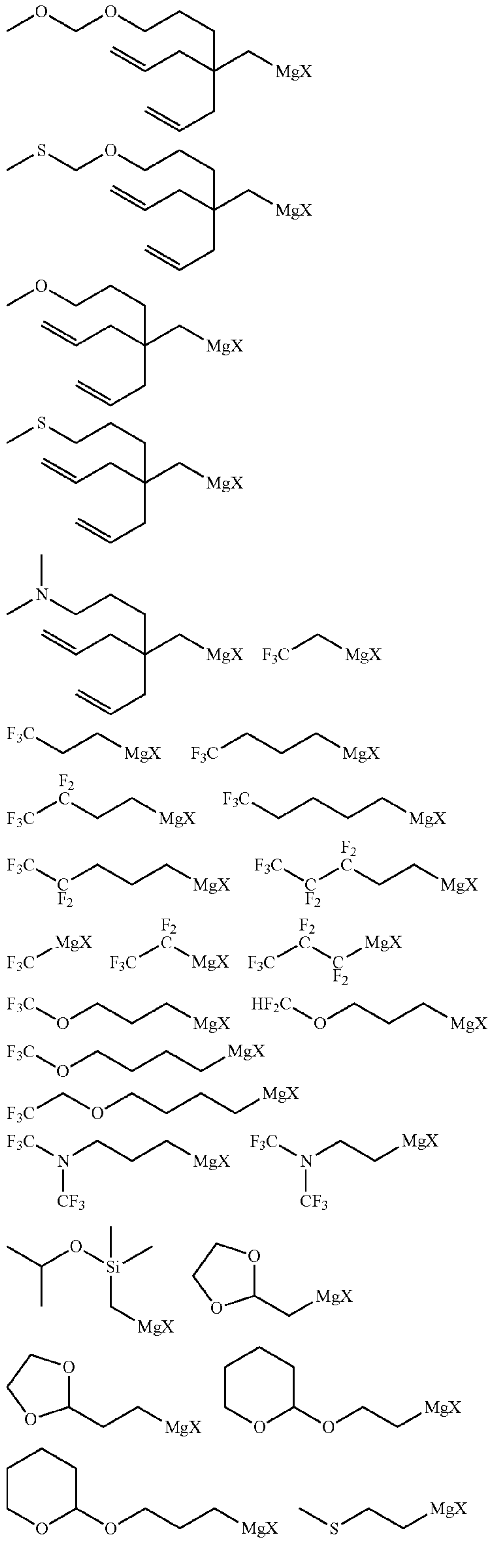
The Grignard reagent can be manufactured, for example, by reacting a formula (B2) below with metal magnesium.

Alternatively, a commercially available product having a desired structure may be used.

R—X Formula (B2)

In the above, R and X are as described above.

In the reaction according to the scheme (1), from the standpoint of improving the yield of the target product, the amount of the Grignard reagent used is preferably from 1 equivalent to 30 equivalent, more preferably from 3 equivalent to 20 equivalent, or even more preferably from 5 equivalent to 15 equivalent with respect to the total number of leaving groups L included in the compound (A).

The transition metal compound can be selected for use, as appropriate, from known catalysts used for the Grignard reaction. The transition metal compound is preferably a compound that includes, as a transition metal, an element in the groups from 3 to 12 of the periodic table, and among those, a compound including an element in the groups from 8 to 11 is preferable. For the element in the groups from 8 to 11, in particular, the compound preferably includes one or more elements selected from copper, nickel, palladium, cobalt, and iron, or more preferably further includes copper.

When the transition metal compound includes copper, this copper may be a zero-valent, monovalent, divalent, or trivalent compound. Yet, from the standpoint of the catalytic activity, in particular, a monovalent or divalent salt or complex salt of copper is preferable. Moreover, from the standpoint of, for example, the availability, copper chloride is more preferable. For the copper chloride, CuCl and $CuCl_2$ can both be used favorably. Herein, the copper chloride may be either anhydride or hydrate. Yet, from the standpoint of the catalytic activity, copper chloride dehydrate is more preferable. The amount of the transition metal compound used is, for example, from 0.1 mol % to 50 mol %, preferably from 1 mol % to 30 mol %, or even more preferably from 2 mol % to 20 mol % with respect to the total number of leaving groups L included in the compound (A).

In the reaction according to the present manufacturing method, a ligand may be used in combination with a transition metal compound that serves as a catalyst, as necessary. The use of a ligand improves the yield of the target product. Meanwhile, the present manufacturing method can provide a sufficient yield even without a ligand, and thus the use of such a ligand is not required.

Examples of the ligand described above include 1,3-butadiene, phenylpropyne, and tetramethylethylenediamine (TMEDA). When a ligand is used, from the standpoint of improving the yield of the target product, the amount of the ligand used is preferably from 0.01 equivalent to 2.0 equivalent or more preferably from 0.1 equivalent to 1.2 equivalent with respect to the total number of leaving groups L included in the compound (A).

The reaction according to the present manufacturing method is normally carried out within a solvent. The solvent can be selected for use, as appropriate, from solvents in which the compound (A) and the Grignard reagent can dissolve. The solvent may be used singly, or a mixed solvent containing two or more types of solvents may be used.

For example, when the compound (A) is a compound having a relatively low content of fluorine atoms (the proportion of fluorine atoms with respect to the molecular weight of the compound molecules), there is no particular limitation on the solvent as long as the solvent is inert to the reaction. Among the solvents that are inert to the reaction, in particular, an ether-based solvent, such as diethyl ether, tetrahydrofuran, or dioxane, is preferable, and tetrahydrofuran is more preferable.

Meanwhile, when the compound (A) is a compound having a relatively high content of fluorine atoms, a mixed solvent containing the aforementioned ether-based solvent and a fluorine-based solvent is preferable.

Examples of the fluorine-based solvent include hydrofluorocarbons (1H,4H-perfluorobutane, 1H-perfluorohexane, 1,1,1,3,3-pentafluorobutane, 1,1,2,2,3,3,4-heptafluorocyclopentane, 2H,3H-perfluoropentane, etc.), hydrochlorofluorocarbons (3,3-dichloro-1,1,1,2,2-pentafluoropropane, 1,3-dichloro-1,1,2,2,3-pentafluoropropane (HCFC-225cb), etc.), hydrofluoroethers ($CF_3CH_2OCF_2CF_2H$ (AE-3000), (perfluorobutoxy)methane, (perfluorobutoxy)ethane, etc.), hydrochlorofluoroolefins ((Z)-1-chloro-2,3,3,4,4,5,5-heptafluoro-1-pentene (HCFO-1437dycc(Z)), (E)-1-chloro-2,3,3,4,4,5,5-heptafluoro-1-pentene (HCFO-1437dycc(E)), (Z)-1-chloro-2,3,3-trifluoro-1-propane (HCFO-1233yd(Z)), (E)-1-chloro-2,3,3-trifluoro-1-propane (HCFO-1233yd(E)), etc.), and fluorine-containing aromatic compounds (perfluorobenzene, m-bis(trifluoromethyl)benzene (SR-solvent), p-bis(trifluoromethyl)benzene, etc.).

The present manufacturing method can be carried out by, for example, preparing a solution containing the compound (A), adding a transition metal compound and a ligand, as necessary, to the solution, and then adding thereto a Grignard reagent solution prepared separately.

The reaction temperature of the compound (A) and the Grignard reagent may be adjusted, as appropriate, in accordance with the combination of the compound (A) and the Grignard reagent. For example, the reaction temperature may be from −20° C. to 66° C. (the boiling point of tetrahydrofuran), and the reaction temperature of from −20° C. to 40° C. is preferable.

EXAMPLES

Now, the present invention will be described in further detail through examples, but the present invention is not limited by these examples. Herein, Example 1, Examples 3 to 10, Example 12, and Example 13 are the examples, and Example 2 and Example 11 are comparative examples.

Synthesis Example: Synthesis of Compound (A1-1)

1H,1H-tridecafluoro-1-heptanol (10.5 g), dichloromethane (100 mL), and triethylamine (6.0 mL) were added and cooled to 0° C. To the above, trifluoromethanesulfonic anhydride (5.6 mL) was added and stirred at room temperature. The resultant was washed with water and then dried with sodium sulfate. The resultant was filtered to remove the solvent, and flash column chromatography involving a silica gel was carried out to obtain 4.73 g of a compound (A1-1) described below.

The result of an NMR measurement of the compound (A1-1) is shown below.

$^1$H-NMR (400 MHz, Chloroform-d) δ 4.84; (t, J=12.3 Hz, 2H). $^{19}$F-NMR (376 MHz, Chloroform-d) δ −74.50; from −81.04; to 81.61; (m), −120.19; (t, J=14.3 Hz), from −122.08; to −122.94; (m), from −122.94; to −123.72; (m), from −126.21; to −126.94; (m).

[Chem. 6]

Compound (A1-1)

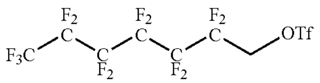

OTf is triflate: —O—S(═O)$_2$(—CF$_3$).

Example 1: Manufacture of Fluorine-Containing Compound (1)

The above compound (A1-1) (241 mg), $CuCl_2$ (12.1 mg), and a 1,3-butadiene THF solution (2.0 M, 0.25 mL) were added and cooled to 10° C. Then, a THF solution of n-butylmagnesium chloride (0.88 M, 5.1 mL) was added dropwise and stirred at room temperature. The resultant was cooled to 0° C., and then a 1 M hydrochloric acid was added to extract with AE-3000. Sodium sulfate was added and dried, and then the resultant was filtered and concentrated. Flash column chromatography involving a silica gel was carried out to obtain 84.0 mg of a fluorine-containing compound (1) described below. Herein, THF stands for tetrahydrofuran.

The result of an NMR measurement of the fluorine-containing compound (1) is shown below.

$^1$H-NMR (400 MHz, Chloroform-d) δ from 2.49; to 1.84; (m, 2H), from 1.63; to 1.11; (m, 6H), from 1.00; to 0.81; (m, 3H).

$^{19}$F-NMR (376 MHz, Chloroform-d) δ−81.57; (t, J=9.7 Hz), −115.20; (ddd, J=18.7, 14.6, 4.6 Hz), −122.73; −123.65; −124.35; −126.92.

[Chem. 7]

Fluorine-Containing Compound (1)

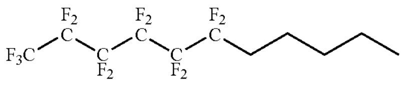

Examples 2 to 9: Method of Manufacturing Fluorine-Containing Compound (1)

Fluorine-containing compounds (1) were manufactured in a manner similar to that of Example 1 except that the loadings of n-butylmagnesium chloride, 1,3-butadiene, and $CuCl_2$ in Example 1 described above were changed as shown in Table 1 below.

Example 10: Method of Manufacturing Fluorine-Containing Compound (1)

A fluorine-containing compound (1) was manufactured in a manner similar to that of Example 1 except that CuCl was used in place of $CuCl_2$ in Example 1 described above and that the loadings were changed as shown in Table 1 below.

Example 11: Manufacturing Fluorine-Containing Compound

The manufacture of a fluorine-containing compound (1) was attempted with the use of a compound (X1) described below.

Triphenylphosphine and carbon tetrabromide were added to 1H,1H-tridecafluoro-1-heptanol and reacted in dichloromethane in an attempt to synthesize the compound (X1) described below. However, this compound (X1) was unstable and was decomposed into alcohol during purification. This revealed that the compound (X1) was not suitable for the synthesis of a fluorine-containing compound (1).

[Chem. 8]

Compound (X1)

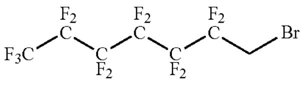

The loading ratio of each component in the syntheses of Example 1 to Example 10 and the yields of the obtained target products are shown in Table 1.

Herein, eq. (equivalent) and mol % in Table 1 are based on the number of triflate groups in the electrophilic reagent. The hyphen (-) in the table indicates that the corresponding component was not added.

Meanwhile, the yield was obtained by quantitating the target product by an internal standard method (internal standard: hexafluorobenzene) by use of $^{19}$F-NMR and was obtained through the following formula. The isolated yield was also obtained for Example 1 (see within the parentheses in Table 1).

Yield=Target Product/Compound (A1-1)×100[%]

TABLE 1

| Examples | Electrophilic Reagent | N-butylmagnesium chloride (eq.) | 1,3-butadiene (eq.) | Transition Metal Compound Type | Transition Metal Compound Loading | Yield (%) |
|---|---|---|---|---|---|---|
| 2 | Compound (A1-1) | 1.0 | — | $CuCl_2$ | — | <1 |
| 3 | Compound (A1-1) | 1.0 | 1.0 | $CuCl_2$ | 2 | 15 |
| 4 | Compound (A1-1) | 3.0 | 1.0 | $CuCl_2$ | 6 | 20 |
| 5 | Compound (A1-1) | 5.0 | 1.0 | $CuCl_2$ | 10 | 32 |
| 6 | Compound (A1-1) | 7.0 | 1.0 | $CuCl_2$ | 14 | 45 |
| 1 | Compound (A1-1) | 9.0 | 1.0 | $CuCl_2$ | 18 | 52 (43) |
| 7 | Compound (A1-1) | 9.0 | 1.0 | $CuCl_2$ | 2 | 51 |
| 8 | Compound (A1-1) | 9.0 | 1.0 | $CuCl_2$ | 1 | 40 |
| 9 | Compound (A1-1) | 9.0 | — | $CuCl_2$ | 2 | 50 |
| 10 | Compound (A1-1) | 1.0 | 1.0 | CuCl | 2 | 14 |

As shown in Table 1, according to the manufacturing method of Example 1 and Examples 3 to 10, which includes reacting the compound (A1-1) that is a compound having a partial structure expressed by the formula (a) described above with a Grignard reagent in the presence of a transition metal compound, a target fluorine-containing compound can be synthesized under a relatively moderate reaction condition.

Examples 12 and 13 described below indicate that various other compounds can be synthesized with the present manufacturing method.

Example 12: Manufacture of Fluorine-Containing Compound (2)

Synthesis Example 12-1: Synthesis of Compound (12-1)

2,2,3,3-tetrafluoro-1,4-butanediol (1.58 g), dichloromethane (100 mL), and pyridine (2.2 mL) were added and cooled to 0° C. To the above, trifluoromethanesulfonic anhydride (7.18 mL) was added and stirred for three hours at room temperature. The resultant was washed twice with water and then dried with sodium sulfate. The resultant was filtered to remove the solvent, and hexane was then added. The above was stirred for 30 minutes, filtered, and dried under reduced pressure to obtain 3.70 g of a compound (12-1) described below.

The result of an NMR measurement of the compound (12-1) is shown below.

$^1$H-NMR (400 MHz, Chloroform-d) δ: from 4.93; to 4.75; (m, 4H).

$^{19}$F-NMR (376 MHz, Chloroform-d) δ: −74.68; from −120.99; to −121.24; (m).

[Chem. 9]

Compound (12-1)

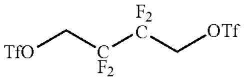

(Synthesis Example 12-2: Synthesis of Fluorine-Containing Compound (2)

The above compound (12-1) (213 mg) and $CuCl_2$ (1.3 mg) were added and cooled to 10° C. Then, a THF solution of n-butylmagnesium chloride (0.88 M, 5.1 mL) was added dropwise and stirred for one hour at room temperature. The resultant was cooled to 0° C., and then a 1 M hydrochloric acid was added to extract with AE-3000. Sodium sulfate was added and dried, and then the resultant was filtered and concentrated. Flash column chromatography involving a silica gel was carried out to obtain 30.1 mg of a fluorine-containing compound (2) described below.

The result of an NMR measurement of the compound (2) is shown below.

$^1$H-NMR (400 MHz, Chloroform-d) δ from 2.17, to 1.88; (m, 4H), from 1.60; to 1.31; (m, 12H), from 0.99; to 0.83; (m, 6H). $^{19}$F-NMR (376 MHz, Chloroform-d) δ: from −116.28; to −116.59; (m).

[Chem. 10]

Compound (2)

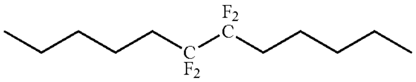

Example 13: Manufacture of Fluorine-Containing Compound (3)

Synthesis Example 13-1: Synthesis of Compound (13-1)

A compound (13-1) described below was obtained through the method disclosed in Example 7 of International Patent Publication No. WO2013/121984.

$CF_3—O—(CF_2CF_2O—CF_2CF_2CF_2CF_2O)_n(CF_2CF_2O)—CF_2CF_2CF_2—CH_2OH$ Formula (13-1)

The mean value of the number of repeating units n is 13.

Synthesis Example 13-2: Synthesis of Compound (13-2)

The above compound (13-1) (6.80 g), 2,6-lutidine (0.759 g), and AE-3000 (28.0 g) were added and stirred at 0° C. To the above, trifluoromethanesulfonic acid anhydride (0.987 g) was added and then stirred at room temperature. The resultant was washed with water to remove the solvent, and flash column chromatography involving a silica gel was carried out to obtain 6.81 g of a compound (13-2) described below.

$CF_3—O—(CF_2CF_2O—CF_2CF_2CF_2CF_2O)_n(CF_2CF_2O)—CF_2CF_2CF_2—CH_2OTf$ Formula (13-2)

The mean value of the number of repeating units n is 13, and OTf is triflate: $—O—S(=O)_2(—CF_3)$.

The NMR spectrum of the compound (13-2);

$^1$H-NMR (400 MHz, Chloroform-d) δ (ppm): 4.78; (t, J=12.3 Hz, 2H).

$^{19}$F-NMR (376 MHz, Chloroform-d) δ (ppm): −55.28; −74.11; −82.86; −88.07; −90.20; −119.84; −125.28; −126.16.

Synthesis Example 13-3: Synthesis of Compound (13-3)

Diethyldiallylmalonate (60.0 g), lithium chloride (23.7 g), water (6.45 g), and dimethyl sulfoxide (263 g) were added and stirred at 160° C. The resultant was cooled to room temperature, added with water, and extracted with ethyl acetate. Hexane was added to an organic layer, and the resultant was washed with a saturated saline solution and dried with sodium sulfate. The resultant was filtered to remove the solvent, and 39.5 g of a compound (13-3) described below was obtained.

[Chem. 11]

Formula (13-3)

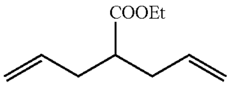

The NMR spectrum of the compound (13-3);

$^1$H-NMR (400 MHz, Chloroform-d) δ (ppm): (ddt, J=17.1, 10.1, 7.0 Hz, 2H), from 5.06; to 4.94; (m, 4H), 4.09; (q, J=7.1 Hz, 2H), 2.47; (ddd, J=14.0, 8.0, 6.1 Hz, 1H), 2.33; (dt, J=14.9, 7.5 Hz, 2H), 2.22; (dt, J=14.1, 6.5 Hz, 2H), 1.21; (t, J=7.1; Hz, 3H).

Synthesis Example 13-4: Synthesis of Compound (13-4)

THF (260 mL) and diisopropylamine (29.8 g) were added, and then the solution was cooled to −78° C. An n-butyllithium hexane solution (2.76 M, 96.6 mL) was added, and the temperature of the resultant was raised to 0° C. The above was stirred and then cooled to −78° C., and a THF solution of lithium diisopropylamide (LDA) was prepared. The above compound (13-3) (39.5 g) was added to the THF solution and stirred. Then, allyl bromide (24.1 mL) was added. The temperature of the resultant was raised to 0° C., and a 1 M hydrochloric acid (100 mL) was added to remove THF under reduced pressure. The above was extracted with dichloromethane, and then sodium sulfate was added. The resultant was filtered to remove the solvent, and flash column chromatography involving a silica gel was carried out to obtain 45.0 g of a compound (13-4).

[Chem. 12]

Formula (13-4)

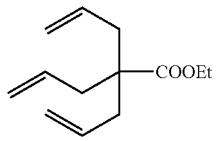

The NMR spectrum of the compound (13-4);

$^1$H-NMR (400 MHz, Chloroform-d) δ (ppm): from 5.74; to 5.62; (m, 3H), 5.04; (dd, J=13.6, 1.9 Hz, 6H), 4.10; (q, J=7.1 Hz, 2H), 2.29; (d, J=7.4 Hz, 6H), 1.22; (t, J=7.1 Hz, 3H).

Synthesis Example 13-5: Synthesis of Compound (13-5)

The above compound (13-4) (45.0 g) was dissolved in THF (620 mL), and the resultant was cooled to 0° C. A THF solution of lithium aluminum hydride (104 mL) was added and stirred. Water and a 15% sodium hydroxide solution were added and stirred at room temperature. Then, the resultant was diluted with dichloromethane. The resultant was filtered to remove the solvent, and flash column chromatography involving a silica gel was carried out to obtain 31.3 g of a compound (13-5) described below.

[Chem. 13]

Formula (13-5)

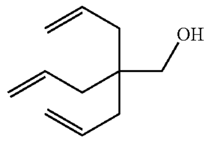

The NMR spectrum of the compound (13-5);

$^1$H-NMR (400 MHz, Chloroform-d) δ (ppm): from 5.90; to 5.76; (m, 3H), from 5.10; to 5.02; (m, 6H), 3.38; (s, 2H), 2.03; (dt, J=7.5, 1.2 Hz, 6H), 1.45; (s, 1H).

Synthesis Example 13-6: Synthesis of Compound (13-6)

Acetonitrile (380 mL), the above compound (13-5) (31.3 g), triphenylphosphine (64.3 g), and carbon tetrachloride (33.9 g) were added and stirred at 90° C. After concentration, ethyl acetate/hexane was added and stirred. The resultant was filtered and concentrated, and then 28.2 g of a compound (13-6) described below was obtained through distillation.

[Chem. 14]

Formula (13-6)

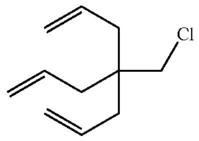

The NMR spectrum of the compound (13-6);

$^1$H-NMR (400 MHz, Chloroform-d) δ (ppm): from 5.83; to 5.67; (m, 3H), from 5.16 to 5.01 (m, 6H), 3.32; (s, 2H), 2.05; (dt, J=7.5; 1.1; Hz, 6H).

Synthesis Example 13-7: Synthesis of Compound (13-7)

THF (35 mL) and iodine (0.180 g) were added to magnesium (2.36 g) and stirred at room temperature. A THF (35 mL) solution of the above compound (13-6) (14.0 g) was added, and the resultant was heated at reflux for two hours to prepare a solution (1.0 M) of a compound (13-7) described below.

[Chem. 15]

Formula (13-7)

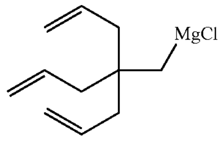

(Synthesis Example 13-8: Synthesis of Fluorine-Containing Compound (3))

$CuCl_2$ (16.0 mg), 1-phenyl-1-propyne (0.052 g), 1,3-bis trifluoromethyl benzene (24 mL), and the above compound (13-1) (4.00 g) were added, and then the above compound (13-7) (5.0 mL, 1.0 M) was added thereto. The resultant was stirred at room temperature, then washed with a 1 M hydrochloric acid, and dried with sodium sulfate. The resultant was filtered to remove the solvent, and AC-6000 was then added. The resultant was washed with MeOH, and then flash column chromatography involving a silica gel was carried out to obtain 0.139 g of a fluorine-containing compound (3) described below. Herein, AC-6000 is $C_6F_{13}C_2H_5$.

[Chem. 16]

Formula (3)

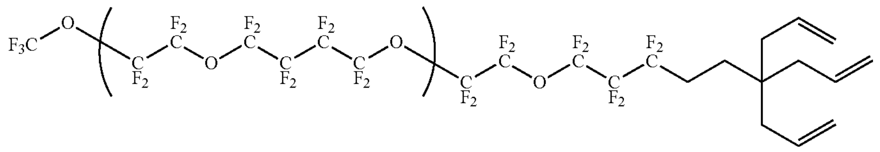

The mean value (n) of the number of repeating units: 10

The NMR spectrum of the compound (3);

$^1$H-NMR (400 MHz, Chloroform-d) δ (ppm): 5.77; (ddt, J=14.9; 10.7; 7.4; Hz, 3H), from 5.07; to 4.99; (m, 6H), from 2.19; to 2.05; (m, 2H), 1.97; (d, J=7.4 Hz, 6H), from 1.59; to 1.50; (m, 2H). $^{19}$F-NMR (376 MHz, Chloroform-d) δ (ppm): −55.29; −82.90; −88.13, −90.24 (d, J=8.0 Hz), −114.62, −125.34, −126.49.

INDUSTRIAL APPLICABILITY

According to the present invention, a fluorine-containing compound that can be used in a variety of fields, including agricultural chemicals, medicines, and intelligent materials, can be synthesized under a relatively moderate reaction condition by use of a readily available compound. Moreover, the use of a Grignard reagent having, for example, a carbon-carbon double bond makes it possible to add a double bond to the compound (A) with ease, and a compound that is useful also as a material for synthesizing various other compounds can be obtained.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A method of manufacturing a fluorine-containing compound, comprising:

reacting a compound of Formula (A1) or Formula (A2), with a Grignard reagent of Formula (B), in the presence of a transition metal compound, and obtaining a fluorine-containing compound of a formula $G^1$-$CF_2$—$CH_2$—R if the starting material is of Formula (A1), or obtaining a fluorine-containing compound of a formula R—$CH_2$(—$CF_2$-$G^2$)$_n$-$CF_2$—$CH_2$—R if the starting material is of Formula (A2), $G^1$-$CF_2$—$CH_2$-L Formula (A1)

L-$CH_2$(—$CF_2$-$G^2$)$_n$-$CF_2$—$CH_2$-L Formula (A2)

R—MgX Formula (B)

wherein $G^1$ is a monovalent group having a (poly)oxyfluoroalkylene chain, a hydrogen atom, an alkyl group, or a fluoroalkyl group, $G^2$ is a divalent group having a (poly)oxyfluoroalkylene chain, a single bond, an alkylene group, or a fluoroalkylene group, L is a sulfonate group, and a plurality of L's in the formula (A2) may be identical to or different from each other, R is a hydrocarbon group optionally including a substituent and/or a heteroatom within a carbon chain, X is a halogen atom, and n is 0 or 1.

2. The method of manufacturing a fluorine-containing compound according to claim 1, wherein $G^1$ is a monovalent group having a (poly)oxyfluoroalkylene chain or a perfluoroalkyl group.

3. The method of manufacturing a fluorine-containing compound according to claim 1, wherein, n is 1, and $G^2$ is a divalent group having a (poly)oxyfluoroalkylene chain, a single bond, or a perfluoroalkylene group.

4. The method of manufacturing a fluorine-containing compound according to claim 1, wherein the Grignard reagent is of Formula (B1), $R^1$—$CH_2$—MgX Formula (B1)

wherein $R^1$ is a hydrogen atom or a hydrocarbon group optionally including a substituent and/or a heteroatom within a carbon chain, and X is a halogen atom.

5. The method of manufacturing a fluorine-containing compound according to claim 1, wherein L is a triflate group.

6. The method of manufacturing a fluorine-containing compound according to claim 1, wherein the transition metal compound comprises copper.

* * * * *